(12) United States Patent
Stock et al.

(10) Patent No.: US 9,138,003 B2
(45) Date of Patent: Sep. 22, 2015

(54) PHOSPHONATES AND DERIVATIVES THEREOF AS ENHANCERS OF THE ACTIVITY OF INSECTICIDES

(75) Inventors: David Stock, Berkshire (DE); Catherine Julia Piper, Berkshire (DE); Julia Lynne Ramsay, Berkshire (DE); Patrick Joseph Mulqueen, Berkshire (DE); Richard Brian Perry, Berkshire (DE); Mark Steven Birchmore, Base (CH)

(73) Assignee: Syngenta Crop Protection Inc., Greensboro, NC (US)

( * ) Notice: Subject to any disclaimer, the term of this patent is extended or adjusted under 35 U.S.C. 154(b) by 1516 days.

(21) Appl. No.: 10/513,640

(22) PCT Filed: May 22, 2003

(86) PCT No.: PCT/GB03/02210
§ 371 (c)(1),
(2), (4) Date: Dec. 7, 2005

(87) PCT Pub. No.: WO03/099012
PCT Pub. Date: Dec. 4, 2003

(65) Prior Publication Data
US 2006/0093637 A1 May 4, 2006

(30) Foreign Application Priority Data
May 23, 2002 (GB) .................................. 0211924.6

(51) Int. Cl.
| | | |
|---|---|---|
| *A01N 25/00* | (2006.01) |
| *A01N 57/10* | (2006.01) |
| *A01N 57/20* | (2006.01) |
| *A01N 47/02* | (2006.01) |
| *A01N 43/90* | (2006.01) |
| *A01N 43/36* | (2006.01) |
| *A01N 51/00* | (2006.01) |
| *A01N 57/14* | (2006.01) |
| *A01N 43/68* | (2006.01) |
| *A01N 53/00* | (2006.01) |
| *A01N 47/38* | (2006.01) |
| *A01N 25/30* | (2006.01) |

(52) U.S. Cl.
CPC ................. *A01N 57/20* (2013.01); *A01N 25/30* (2013.01); *A01N 43/36* (2013.01); *A01N 43/68* (2013.01); *A01N 43/90* (2013.01); *A01N 47/02* (2013.01); *A01N 47/38* (2013.01); *A01N 51/00* (2013.01); *A01N 53/00* (2013.01); *A01N 57/14* (2013.01)

(58) Field of Classification Search
CPC ... A01N 57/20; A01N 2300/00; A01N 43/22; A01N 43/36; A01N 43/68; A01N 43/90; A01N 47/02; A01N 47/38; A01N 51/00; A01N 53/00; A01N 57/14; A01N 25/30
See application file for complete search history.

(56) References Cited

U.S. PATENT DOCUMENTS

| | | | |
|---|---|---|---|
| 4,976,769 A | 12/1990 | Iwasaki | |
| 5,451,562 A * | 9/1995 | Rusch | ............ 504/127 |
| 5,876,739 A * | 3/1999 | Turnblad et al. | ............. 424/408 |
| 6,093,679 A | 7/2000 | Azuma et al. | |
| 6,939,830 B1 * | 9/2005 | Gaulliard et al. | ............. 504/253 |

FOREIGN PATENT DOCUMENTS

| | | |
|---|---|---|
| EP | 0025179 | 3/1981 |
| WO | 9418837 | 9/1994 |
| WO | 9603879 | 2/1996 |

* cited by examiner

*Primary Examiner* — Kyle Purdy
(74) *Attorney, Agent, or Firm* — James Cueva

(57) ABSTRACT

An insecticidal composition having as an adjuvant a phosphonate or an alkoxylated derivative or dimer thereof. Preferred phosphonates are bis-(2-ethylhexyl)-2ethylhexylphosphonate, bis-(2-ethylhexyl)-octylphosphonate and bis-(butyl)butylphosphonate.

4 Claims, No Drawings

PHOSPHONATES AND DERIVATIVES THEREOF AS ENHANCERS OF THE ACTIVITY OF INSECTICIDES

This application is a 371 of International Application No. PCT/GB03/02210 filed May 22, 2003, which claims priority to GB 0211924.6, filed May 23, 2002, the contents of which are incorporated herein by reference.

The present invention relates to a composition and in particular to an insecticidal composition, more particularly an insecticidal composition containing an organic phosphonate adjuvant.

U.S. Pat. No. 2,927,014 discloses the use of a range of organic phosphonate and phosphinate compounds as herbicides. WO 9304585 discloses the use of certain organic phosphinate and phosphonate compounds as adjuvants to enhance the activity of certain herbicides. WO 9418837 teaches the use of a specific phosphonate, bis(2-ethyl hexyl) 2-ethylhexyl phosphonate, as adjuvant to improve the bioperformance of specified herbicides. In WO9800021 there is disclosed that certain phosphonate or phosphinate compounds provide improved fungicidal activity in combination with certain fungicides such as fluquinconazole and azoxystrobin.

The applicants have now found that insecticide activity can be surprisingly enhanced by the use of an organic phosphonate adjuvant.

According to the present invention there is provided an insecticidal composition comprising an insecticide and a phosphonate or an alkoxylated derivative or dimer thereof having the formula (I)

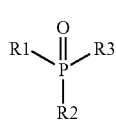

(I)

wherein $R^1$ and $R^2$ are independently an alkoxy group containing from 4 to 20 carbon atoms or a group —[OCH$_2$CHR$^4$]$_n$—OR$^5$ wherein $R^4$ is hydrogen, methyl or ethyl, n is from 0 to 50 and $R^5$ is hydrogen or an alkyl group containing from 1 to 20 carbon atoms; and $R^3$ is (i) an alkyl or alkenyl group containing from 4 to 20 carbon atoms (ii) optionally substituted phenyl or (iii) a group of formula (II)

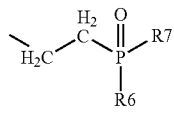

(II)

wherein $R^6$ is an alkoxy group containing from 4 to 20 carbon atoms or a group —[OCH$_2$CHR$^4$]$_n$—OR$^5$ as herein defined and $R^7$ an alkoxy group containing from 4 to 20 carbon atoms or a group —[OCH$_2$CHR$^4$]$_n$—OR$^5$ as herein defined.

The term "alkyl" as used herein, including when used in expressions such as "alkoxy" includes linear or branched chain alkyl groups. Optional substituents which may be present in optionally substituted phenyl include $C_{1-4}$ alkyl and halogen.

Certain compounds of formula (I) may contain or exist in the form of dimers and such dimers are included in the scope of the present invention.

Optional alkoxylation of an ester group is represented by the group —[OCH$_2$CHR$^4$]$_n$—OR$^5$ as herein defined. It is preferred that the value of n is from 0 to 10 and more preferably from 0 to 5. If a range of degrees of alkoxylation is present, n may represent an average value and is not necessarily an integer. Similarly, mixed alkoxylation may take place such that different values of $R^4$ are present in the group —[OCH$_2$CHR$^4$]$_n$. It is preferred that $R^5$ is an alkyl group containing from 1 to 8 carbon atoms. If n is 0, the group —[OCH$_2$CHR$^4$]$_n$—OR$^5$ becomes alkoxy and when n is 0 therefore the group —OR$^5$ is suitably alkoxy containing from 4 to 20 carbon atoms.

It is preferred that each of the groups $R^1$ and $R^2$ are alkoxy groups containing from 4 to 10 carbon atoms and $R^3$ is an alkyl group containing from 4 to 10 carbon atoms. Suitable phosphonates are disclosed in WO 98/00021 and the present invention also includes equivalents wherein the relevant alkyl chain length is lower than that disclosed in WO 98/00021. It is especially preferred that each of $R^1$, $R^2$ and $R^3$ contain from 4 to 8 carbon atoms. Preferred phosphonates are bis-(2-ethylhexyl)-2-ethylhexylphosphonate, bis-(2-ethylhexyl)-octylphosphonate and bis-(butyl)-butylphosphonate.

The compositions of the invention may also contain mixtures. Thus the compositions may comprise two or more organic phosphonate compounds of the invention and/or other additives (normally termed adjuvants) which can be surfactants and/or oils.

The insecticidal active ingredient in the composition of the invention may include one or more of:

(a) Acetylcholine Esterase Inhibitors. These work as inhibitors of acetylcholine esterase. Acetylcholine esterase cleaves the ester functionality of the neurotransmitter acetylcholine in the CNS hence preventing repeated stimulation of the acetylcholine receptor. The enzyme has a nucleophilic serine residue at the active site which catalyses the hydrolysis of the ester, generating choline and the acetylated enzyme which is rapidly hydrolysed back to its active form. The insecticidal acetylcholine esterase inhibitors acylate this serine residue with a group which is hydrolysed at a much slower rate than acetate, hence blocking the action of this enzyme. This results in hyperexcitation of the insect cholinergic nervous system resulting in convulsions and death. Representative insecticides having this mode of action include organophosphorus insecticides.

Organophosphorus insecticides are divided into six subclasses according to the exact nature of the phosphorus functional group (phosphates, phosphonates, phosphoramidates, phosphorothiolates, phosphorothioates and phosphorodithiolates), but all contain an electrophilic phosphorus atom with a good leaving group attached. They can also be classified by the nature of the leaving group (aliphatic, phenoxy or aryloxy). The P=S compounds are metabolised in insects to P=O compounds which are much more active, whereas mammals tend to cleave the P—OR bonds more rapidly leading to greater selectivity. Specific examples include chlorpyrifos, pirimiphos-methyl, diazinon, profenofos, methidathion, terbufos dimethoate and fozthiazate and carbamate insecticides such as pirimicarb, benfuracarb, carbaryl and aldicarb;

(b) Acetylcholine Agonists

Acetylcholine is a major neurotransmitter in the CNS, responsible for passing on nerve impulses at synapses and it also mediates muscle stimulation at the nerve-muscle interface. Two major sub-types of the acetylcholine receptor have been classified according to which natural product binds best—muscarine or nicotine. A series of insecticides are available which act by this mechanism and include the nitromethylenes which are of relatively low toxicity to mammals but show potent, broad-spectrum activity on insects with systemic activity. Nitromethylenes are active on both sucking and chewing pests and are active both through stomach and contact action. These nitromethylene insecticides (also called neo-nicotinoids) include imidacloprid, acetamiprid, nitenpyram, clothianidin, thiacloprid, thiamethoxam, MTI-446 (from Mitsui). Another chemical in this class is spinosad which is a mixture of spinosyn and spinosyn B. The spinosyns also act at the nicotinic receptor, though the effects they produce are somewhat different to that of the nitromethylenes;

(c) Chloride Channel Disruptors

These compounds work by disrupting the action of gamma-aminobutyric acid (GABA), the major inhibitory neurotransmitter in the CNS. GABA is released from the pre-synaptic membrane and crosses the synapse where it binds to the GABA receptor. This receptor is coupled to a chloride ion channel that is opened in the presence of GABA. This opening allows the net influx of chloride ions into the polarised nerve cell hence reducing the potential across the nerve membrane (since at rest the inside of the nerve membrane is more positive than the outside). This means that when the nerve fires, the change in potential is smaller than in the absence of GABA and hence the nerve impulse is effectively dampened.

GABA agonists include the avermectins that are macrocyclic natural products that can disrupt a variety of chloride ion channels. They actually mimic the action of GABA resulting in permanent opening of the chloride ion channels resulting in insect paralysis. Abamectin, emamectin (usually as a salt form) and milbemectin are examples of this chemistry. Examples of GABA antagonists include the fiprils exemplified by fipronil and the older compounds such as the "cyclodiene" organochlorine compounds such as endosulfan.

d) Sodium Channel Disruptors

Sodium channels are vital for nerve transmission. At rest a nerve membrane will have a potential difference of approximately 60 mV across it by virtue of the fact that there are more sodium ions on the outside than on the inside. When a nerve impulse travels along the cell, sodium ion channels open in the membrane allowing sodium ions to flood into the cell inducing a positive peak of potential to flow along the nerve cell. Normally these channels close very quickly and sodium ions are pumped out of the cell to restore the resting potential. Sodium channel disruptors hold these channels open for longer periods preventing re-polarisation. Type-1 pyrethroids (and veratrum alkaloids) prevent re-polarisation for 0.01-0.1 seconds, which results in multiple-spike firing of neurons leading to convulsions, whereas type-II pyrethroids can prevent re-polarisation for minutes or longer leading to lack of coordination. Pyrethroid chemistries are examples of this mode of action. Pyrethroids are synthetic analogues of natural products from Chrysanthemum flowers of which pyrethrin-I is typical. They can be classed into two types according to the alcohol portion. Type-I pyrethroids are the first generation and tend to be rather photochemically unstable. Type-II pyrethroids are derived from gamma-cyano-3-phenoxybenzyl alcohol and are about 10× more potent. Some type-II pyrethroids can have an altered acid portion too, incorporating a phenyl ring. This chemistry includes tefluthrin, permethrin, bifenthrin, α-cypermethrin, deltamethrin, β-cyfluthrin, lambda-cyhalothrin, gamma-cyhalotlrin, esfenvalerate and tau-fluvalinate. Other Na channel disruptors include Indoxacarb;

(e) Respiration ihibitors

These include chemical classes such as (i) Site-1 inhibitors for example fenpyroximate, fenazaquin, tebufenpyrad, tolfenpyrad and pyrimidifen and uncouplers. Uncouplers have the effect of uncoupling respiration from ATP production. The proteins in the respiratory electron transport chain use the energy produced from respiration to pump protons across the inner mitochondrial membrane. ATP synthase then uses this pH gradient to drive the synthesis of ATP. Uncouplers are lipophilic weak acids that are able to diffuse through membranes in both neutral and anionic forms and hence can ferry protons across the inner mitochondrial membrane. This destroys the pH gradient and hence removes the driving force for ATP synthesis. Chlorfenapyr is an example of an insecticide of this type;

(f) Octopamine Agonists

Octopamine is another neurotransmitter in the insect CNS (not present in vertebrates). It regulates behavioural arousal in the insect. Octopamine binding to the receptor leads to the increased production of c-AMP, which initiates neuronal excitation. Amidines cause over stimulation of these processes resulting in behaviour such as convulsions and continuous flight.

An example of an octopamine agonist is Amitraz;

(g) Insect growth regulators—IGR's

Benzoyl ureas are examples of this mode of action. These compounds inhibit the biosynthesis of chitin, the polysaccharide that is the major structural component (~50%) of insect exoskeleta. When the insect comes to moult, in the presence of these compounds there is insufficient chitin to complete the construction of the new exoskeleton and hence the insect will die during or immediately after moult. These compounds are not actually "growth regulators" in a hormonal sense, but the term was coined due to the misshapen bodies of the dead insects treated with these compounds. These compounds work best on insects that moult often (e.g. lepidoptera), but their use has been limited because they are only taken up by ingestion and activity is growth stage dependent hence they tend to be slow acting. However this also leads to a very clean environmental toxicity profile and hence these compounds are often used in IPM programs. Examples of insecticides of this class include diflubenzuron, flufenoxuron, chlorfluazuron, hexaflumuron, lufenuron, and novaluron. Others insect growth regulator chemistries (with different effects to the benzoyl ureas) include buprofezin, pyriproxyfen, cyromazine, tebufenoside, methoxyfenoside and etoxazole;

(h) Other Modes of Action

In this sector there are a number of significant insecticide chemistries which have new modes of action (or ill-defined modes of action). These include diafenthiuron, pymetrozine and propargite.

Preferred insecticides include chlorpyrifos, profenofos, pirimicarb, imidacloprid, acetamiprid, nitenpyram, clothianidin, thiacloprid, thiamethoxam, MTI-446 (from Mitsui), spinosad, abamectin, emamectin benzoate, fipronil, λ-cyhalothrin, χ-cyhalothrin, indoxacarb, fenpyroximate, tebufenpyrad, chlorfenapyr, lufenuron, cyromazine, diafenthiuron, and pymetrozine. Compositions of the present invention are particularly suitable for the insecticides thiamethoxam, spinosad, abamectin, emamectin, benzoate, fipronil, lambda-cyhalothrin, gamma-cyhalothrin indoxacarb, fenpyroximate, tebufenpyrad, chlorfenapyr, lufenuron, cyromazine, diafenthiuron, and pymetrozine.

The compositions of the invention may contain an active ingredient that is capable of systemic movement in the plant or a contact insecticide, particularly if the pest targets are cryptic feeders (such as leaf miner).

The compositions are particularly useful in combating certain insect classes such as chewing pests for example Lepidoptora, and sucking pests such as aphid spp.

Surprisingly it has been found that the compositions of the invention have no undue phtototoxic effects on host plants at acceptable rates of use.

Both mixtures of compounds of formula (I) and mixtures of insecticides may be used in the composition of the present invention. Compositions of the present invention may contain further additives conventionally incorporated in insecticidal compositions including further adjuvant(s) such as surfactants and insecticide synergists or other components such as anti-freeze agents, polymers, stickers, photoprotectants, mineral oils, plant oils and derivatives. A number of insecticide synergysts are known to those skilled in the art and a specific example is piperonyl butoxide.

The compound of formula (I) may be added to an insecticidal composition at the tank mix stage and compositions of the invention include such tank-mix compositions which are dilute and ready for application. Alternatively the compound of formula (I) may be incorporated into a concentrated composition that is designed to be diluted prior to application. The nature of the compound of formula (I) may vary depending on the nature of the substituents from a liquid to a solid and from slightly water soluble to highly water insoluble. One skilled in the art will be able to use conventional techniques to provide compositions of the invention which are for example solids or liquids carried on a suitable solid support, including for example wettable powders (WP or SP-soluble powder), wettable granules (WG-water dispersible granule or SG-soluble granule), dispersions of solids or liquids in liquids such as suspension concentrates, oil based suspension concentrates, oil flowables, such as SC (suspension concentrate) or OF (oil miscible flowable), emulsions and mixtures such as EW (emulsion in water), EO (emulsion in oil), SE (supension-emulsion), solutions such as EC (emulsifiable concentrate), DC (dispersible concentrate), UL (ultra-low volume liquid), SL (soluble liquid) and special formulations such as microencapsulated compositions. Preferred compounds of formula (I) are generally oily liquids with limited water solubility. These can therefore be easily incorporated into solutions in oils by typical mixing, optionally in combination with one or more emulsifiers or absorbed onto solid carriers such as clays or silicas for incorporation into dry products. Similarly, compounds of formula (I) which are oily liquids may be used to prepare dispersions of an insecticide in the compound of formula (I) or to prepare solutions containing the compound of formula (I) and an insecticide or to prepare mixed dispersion systems where for example the insecticide is present as a suspension concentrate and the compound of formula (I) is present as an oil-in-water emulsion. Other combinations will occur to those skilled in the art.

Adjuvants are normally applied as a percentage of the spray volume applied per hectare. Water volume per hectare is normally about 200l/ha but can vary from 50 to greater than 3000 for special applications in top fruit. Adjuvants are nominally applied at volumes of from 0.05% to 1.0% of the spray volume per hectare. Taking 200 l/ha as an average, typical rates of adjuvant will therefore be in the region of 10 g (0.05%) to 2000 g (1.0%) per hectare. Typical insecticide rates range from 10 g/ha to 5 kg. Therefore one skilled in the art will expect ratios which cover these typical use rates for both active and adjuvant. These relate directly to ratio (by weight) of insecticide to the compound of formula (I) from 50:1 to 1:400. It is preferred that ratio by weight of the insecticide to the compound of formula (I) is from 25:1 and 1:25 and especially 10:1 and 1:10.

Although it is contemplated that these compositions will generally be applied diluted in water for application to a target crop, the scope of the present invention includes the use of formulations of the invention in ultra-low-volume form, for example in arid areas. The compositions of the invention may also be used for example in bark penetration formulations where there is a desire to enable rapid penetration of an insecticide through tree bark. In addition the compositions of the invention may be used for the treatment and protection of plant seeds using formulations known to the skilled person.

The present invention is illustrated by the following Examples.

EXAMPLE 1

The activity of a range of insecticides combined with 0.5% bis(2-ethylhexyl)-2-ethylhexyl phosphonate (BEEP) was compared with a corresponding formulation containing no bis(2-ethylhexyl)-2-ethylhexyl phosphonate in a test of curative control of L1/L2 *Liriomyza huidobriensis*, leaf miner. The results are set out in Table 1 and show % control of this leaf miner within bean leaves.

TABLE 1

| Rate ppm | thiamethoxam | | chlorfenpyr | | Fipronil | | spinosad | |
|---|---|---|---|---|---|---|---|---|
| | Alone | +BEEP | Alone | +BEEP | Alone | +BEEP | Alone | +BEEP |
| Control | 0 | 0 | 0 | 0 | 0 | 0 | 0 | 0 |
| 400 | 0 | 20 | 0 | 100 | 60 | 100 | 42 | 100 |
| 600 | 0 | 43 | 15 | 100 | 69 | 100 | 73 | 100 |
| 800 | 0 | 63 | 0 | 100 | 66 | 100 | 82 | 100 |
| 1000 | 12 | 68 | 28 | 100 | 83 | 100 | 81 | 100 |

| Rate ppm | Abamectin | |
|---|---|---|
| | Alone | +BEEP |
| Control | 0 | 0 |
| 3.13 | 27 | 99 |
| 6.25 | 48 | 100 |
| 12.5 | 74 | 100 |
| 25 | 96 | 100 |

TABLE 1-continued

| Rate | cypromazine | |
| --- | --- | --- |
| ppm | Alone | +BEEP |
| Control | 0 | 0 |
| 25 | 27 | 28 |
| 50 | 57 | 83 |
| 100 | 81 | 100 |
| 200 | 100 | 100 |

EXAMPLE 2

The activity of lambda-cyhalothrin, profenofos and indoxacarb combined with 0.5% bis(2-ethylhexyl)-2-ethylhexyl phosphonate (BEEP) was compared with a corresponding formulation containing no bis(2-ethylhexyl)-2-ethylhexyl phosphonate in a feeding/contact test against *Plutella xylostella*. The results are set out in Table 2 and show % control.

TABLE 2

| | Lambda-cyhalothrin | |
| --- | --- | --- |
| Rate | Alone | +BEEP |
| Control | 21 | 11 |
| 0.31 ppm | 54 | 100 |
| 0.63 ppm | 66 | 100 |
| 1.25 ppm | 83 | 100 |
| 2.5 ppm | 95 | 100 |

| | Profenofos | |
| --- | --- | --- |
| Rate | Alone | +BEEP |
| Control | 21 | 11 |
| 12.5 ppm | 16 | 65 |
| 25 ppm | 41 | 95 |
| 50 ppm | 95 | 100 |
| 100 ppm | 100 | 100 |

| | Indoxacarb | |
| --- | --- | --- |
| Rate | Alone | +BEEP |
| Control | 15 | 20 |
| 0.16 ppm | 32 | 57 |
| 0.31 ppm | 26 | 80 |
| 0.63 ppm | 32 | 98 |
| 1.25 ppm | 80 | 100 |

EXAMPLE 3

The activity of lambda-cyhalothrin, as Karate 10CS with 0.5% bis(2-ethylhexyl)-2-ethylhexyl phosphonate (BEEP) was compared with a Karate 10CS containing no bis(2-ethylhexyl)-2-ethylhexyl phosphonate in a translaminar test (3 day assessment time) against R2 *Myzus persicae*. The results are set out in Table 3 and show % control.

TABLE 3

| | Lambda-cyhalothrin as Karate 10 CS | |
| --- | --- | --- |
| Rate ppm | Alone | +BEEP |
| Control | 10 | 4 |
| 62 | 41 | 72 |
| 125 | 45 | 98 |
| 250 | 26 | 98 |

EXAMPLE 4

The activity of thiamethoxam as Actara 25WG with bis(2-ethylhexyl) octyl phosphonate (BEOP) at 0.5% was compared with Actara containing no bis(2-ethylhexyl) octyl phosphonate in a translaminar test (3 day assessment time) against *Aphis gossypii*. The results are set out in Table 4 and show % control.

TABLE 4

| | thiamethoxam as Actara 25 WG | |
| --- | --- | --- |
| Rate ppm | Alone | +BEOP |
| Control | 11 | 3 |
| 15.6 | 45 | 45 |
| 31.2 | 68 | 48 |
| 62.5 | 72 | 96 |

The invention claimed is:

1. A method of enhancing activity of an insecticidal composition comprising adding to the insecticidal composition, bis-(2-ethylhexyl)-2-ethylhexylphosphonate.

2. The method according to claim 1 wherein the insecticidal composition comprises an insecticide selected from chlorpyrifos, profenofos, pirimicarb, imidacloprid, acetamiprid, nitenpyram, clothianidin, thiacloprid, thiamethoxam, MTI-446, spinosad, abamectin, emamectin benzoate, fipronil, lambda-cyhalothrin, gamma-cyhalothrin, indoxacarb, fenpyroximate, tebufenpyrad, chlorfenapyr, lufenuron, cyromazine, diafenthiuron, and pymetrozine.

3. The method according to claim 2 wherein the insecticide is selected from imidacloprid, clothianidin and thiamethoxam.

4. The method according to claim 3 wherein the insecticide is thiamethoxam.

* * * * *